(12) United States Patent
Brookes et al.

(10) Patent No.: US 6,235,534 B1
(45) Date of Patent: May 22, 2001

(54) INCREMENTAL ABSORBANCE SCANNING OF LIQUID IN DISPENSING TIPS

(76) Inventors: Ronald Frederich Brookes; Merrit Nyles Jacobs; Alan John Lowne; James David Shaw, all of Ortho-Clinical Diagnostics, Inc., Rochester, NY (US) 14626-5101

( * ) Notice: Subject to any disclaimer, the term of this patent is extended or adjusted under 35 U.S.C. 154(b) by 0 days.

(21) Appl. No.: 09/264,806

(22) Filed: Mar. 9, 1999

Related U.S. Application Data (60) Provisional application No. 60/083,208, filed on Apr. 27, 1998.

(51) Int. Cl.[7] .......................... G01N 21/00; G01N 35/08; G01N 21/27; B01L 3/02; G01D 11/26
(52) U.S. Cl. ..................... 436/164; 436/54; 422/100; 422/82.09; 422/119
(58) Field of Search ................... 422/100, 82.09, 422/119; 436/54, 164; 250/222.2, 573, 574

(56) References Cited

U.S. PATENT DOCUMENTS

| | | |
|---|---|---|
| 5,380,666 | 1/1995 | Wuerschum . |
| 5,463,228 | 10/1995 | Krause . |
| 5,575,977 * | 11/1996 | McKinney et al. ............ 422/73 |
| 5,906,795 * | 5/1999 | Nakashima et al. ............ 422/100 |
| 5,919,706 * | 7/1999 | Tajima ............ 436/54 |
| 5,955,378 * | 9/1999 | Challener ............ 436/525 |
| 6,113,858 * | 9/2000 | Tang et al. ............ 422/82.09 |

OTHER PUBLICATIONS

European Search Report EP 99 30 3195 Date of Completion of Search Jul. 17, 2000.
Patent Abstracts of Japan vol. 007, No. 010 (P–168), Jan. 14, 1983—&U JP 57 168165 A (Nippon Tectron KK), Oct. 16, 1982.
Patent Abstracts of Japan vol. 009, No. 232 (P–389), Sep. 18, 1985 & JP 60 086439 A (Toshiba KK), May 16, 1985.

* cited by examiner

Primary Examiner—Lyle A. Alexander
Assistant Examiner—Brian R. Gordon (57) ABSTRACT

A method and apparatus for detecting improper liquid content of a metering tip of an analyzer. The method detects the content or status using radiation between 630 and 2000 nm, and comprises the steps of: a) aspirating the liquid into the tips; b) scanning the liquid; c) providing relative motion between the tip and the scanner while simultaneously scanning the liquid; d) detecting the amount of light transmitted to detector at all levels of the liquid; e) comparing the detected light with light known to be transmitted at levels of liquid free of air bubbles; and flagging the results.

11 Claims, 9 Drawing Sheets

INCREMENTAL ABSORBANCE SCANNING OF LIQUID IN DISPENSING TIPS

This application claim benefit to Provisional Application No. 60/083,208 filed Apr. 27, 1998.

FIELD OF THE INVENTION

This invention relates to methods and apparatus for detecting improper amounts of liquid in a dispensing tip, and/or liquid at improper places in the tip.

BACKGROUND OF THE INVENTION

It is conventional to test blood donated to a blood bank by dispensing it from a pipette tip into wells of a microtiter plate for reaction to determine the presence of an infectious disease. It is critical in these tests that the correct amount of blood be dispensed, no more and no less. That in turn is dictated in part by the proper volume of blood being aspirated into the tip prior to dispensing. Such a pipette tip is provided with a conductive plunger that senses the level of liquid in the primary container. After aspiration, although it can detect liquid in the tip prior to withdrawing from the primary container, it cannot determine the condition of the liquid, that is, if it has bubbles. The reason is that air bubbles are surrounded by liquid and are still conductive.

Such a conventional system has worked well in most instances. There are isolated examples, however, when that system does not adequately detect improper dispensing:

a) if blood sample hangs from the tip as a pendant drop following aspiration or dispensing, or b) if air bubbles or the like have been aspirated into the tip so that the sample aspirated is less than expected because of the air bubble(s), or c) the liquid is forced above the plunger.

Condition (a) is a problem following aspiration because the nominal volume is present in the tip, plus an additional volume is present pendant from the tip. That additional volume gets added to the nominal volume at the next dispensing, so as to alter significantly the volume to be tested. It must be noted that the problem of the pendant drop can occur after dispensing as well—if all or a portion of the dispensed volume perfuses up the exterior side of the tip during dispensing, and remains there as a pendant drop after dispensing, the volume intended to have been so dispensed into a well for testing will be short by the amount of the perfused drop(s). Condition a) can also be indicative of a clot having formed from fibrin, now in or on the tip, which can also cause air bubbles in the tip. Similarly, c) is caused by clotting so that the dispensing pressure forces liquid above the plunger.

Condition (b) is a problem because, contrary to the result detected by the conductive plunger, insufficient volume is actually present for dispensing, as represented by the volume of the air bubble(s).

Other solutions have been considered but are unsatisfactory. The use of a pressure transducer, to track tell-tale pressure changes during metering, is not feasible due to the presence of the conductive plunger within the tip. The use of a digital camera to record images of the tip for comparison of the raw data against a "visual standard" is expensive and imprecise. Visual inspection is obscured by the optical complexities of the tip. Lipemic, hemolytic or icteric samples can visually obscure bubbles.

Accordingly, there has been a significant need prior to this invention to improve the detection of improper aspiration/ dispensing of blood samples for such things as blood bank testing.

SUMMARY OF THE INVENTION

We have devised a method and apparatus that improve such detection of improper aspiration/dispensing.

More specifically, in accord with one aspect of the invention, there is provided a method of detecting the status of aqueous liquid in a dispensing tip having an axis of symmetry and which is capable of transmitting light therethrough of radiation between 630 and 2000 nm, comprising the steps of:

a) aspirating the liquid into one of the tips to fill the tip to a nominal level;

b) scanning the liquid in the tip by a scanner comprising a light source and a light detector, the source and detector being aligned along a direction that is generally normal to the tip axis;

c) providing relative motion between the tip and the scanner while step b) is conducted, so that the scanner scans from a first position below the tip where a pendant drop of the aqueous liquid would be located if present, to a predetermined second position above the first position that represents the nominal level;

d) while conducting steps b) and c), separately detecting at each of several portions of the tip between and including the first and second positions, the amount of light transmitted to the detector, so that all liquid-containing levels within the tip are detected;

e) comparing the detected light of step d) with light known to be transmitted if liquid is present only at all of the levels, free of air bubbles; and f) flagging the results as being in error if water is detected at the first position, free of air bubbles, or if it is not detected at any one of the levels within the tip up to and including the second position; or if it is detected above the second position.

In accord with another aspect of the invention, there is provided apparatus for detecting improper liquid content of a metering tip of an analyzer, the tip having an axis, the apparatus comprising:

a) a scanner comprising a light source, a light detector, and means for transmitting light from the source to the detector at a wavelength which is between about 630 and about 2000 nm;

b) moving means for providing relative motion of one of the tips past the scanner so that the scanner scans the tip and its contents;

c) a controller of the moving means and the detector that directs the detector to detect light transmitted through the tip to the detector at at least several adjacent portions of the tip, as well as just below the tip where any pendant drop would be located; and d) a comparator that compares the light transmitted at the several levels with that known to represent the tip containing bubble-free liquid at each of the levels.

Accordingly, it is an advantageous feature of the invention that improper dispensing from tips due to errors in aspirating or dispensing, can be detected, even in the presence of an opaque plunger that contacts the liquid for conductivity testing.

Other advantageous features will be apparent upon reference to the following Detailed Description, when read in light of the attached drawings.

DETAILED DESCRIPTION OF THE PREFERRED EMBODIMENTS

The invention is hereinafter described with respect to the preferred embodiments, wherein a conductive, opaque plunger is included within the tip, and the liquid aspirated is whole blood for testing at blood banks. In addition, the invention is applicable regardless of the kind of tip used to aspirate and dispense, whether or not a plunger is present, and regardless of the liquid involved and its testing, provided that the nature of the tip and the liquids tends to interfere with an inspection done visually only, i.e., by eye or by a digital camera.

Figure 2:
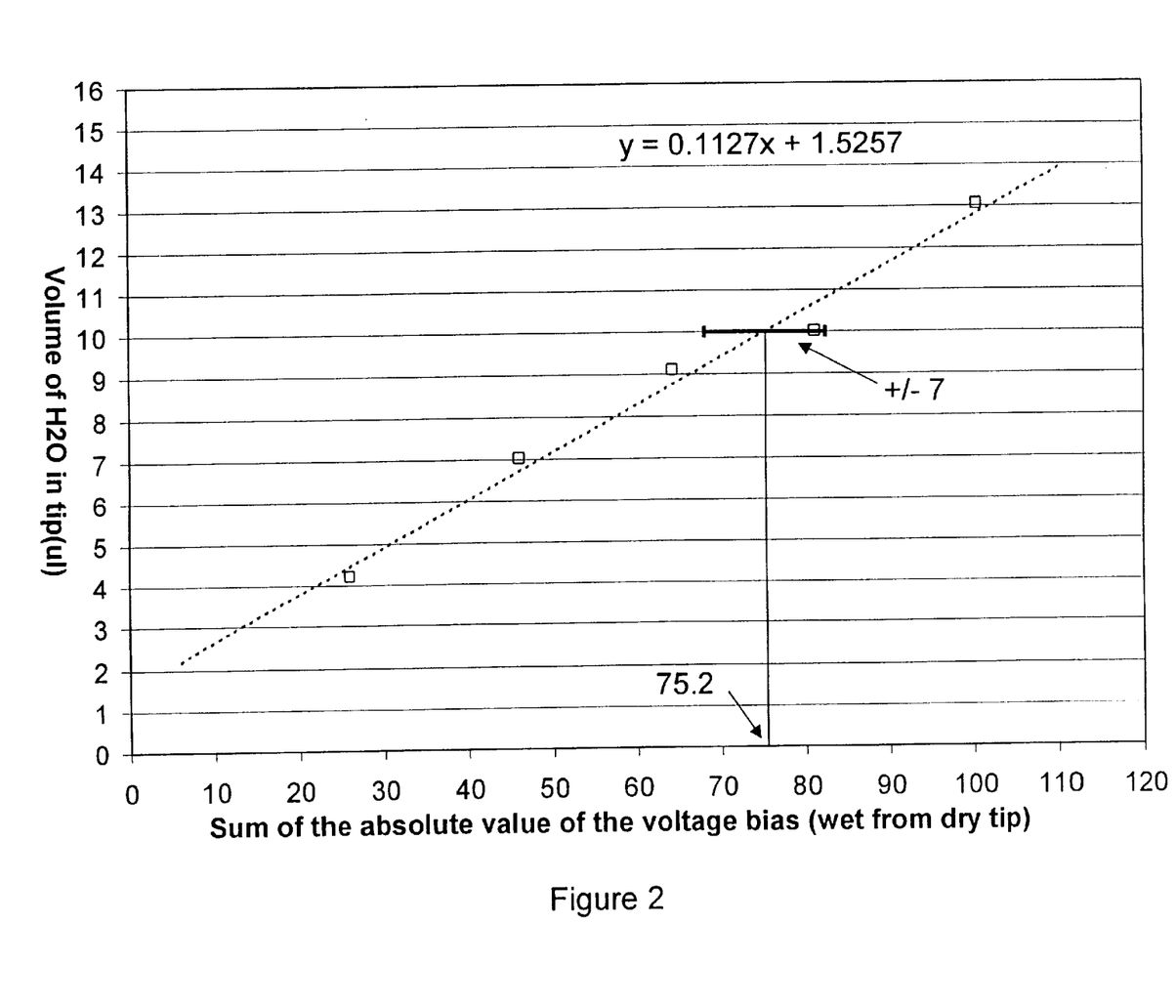
FIG. 2 is a plot of fluid volume within the tip against transmitted light radiation detected when the tip is properly filled, after having subtracted therefrom the light transmitted through the tip with no liquid present.

In brief, the process of the invention comprises separately detecting the amount of light transmitted through several portions of the tip when the liquid is present during use, that is, by incremental scanning, and comparing that with the light known to be transmitted if only the liquid is present only where it should be present. In practice, this is done preferably in two alternative ways—one represented by FIG. 2 is by subtracting from the "unknown" image a "blank" which is the values of light transmitted through the same tip with no liquid present, and integrating each of the several portions to provide an overall summed absolute value, and then comparing that value against a calibrated table or curve of values created with more or less air bubbles present.

As used herein, "integrating" or "integration" refers to summing broadly the transmission values over all the pixels representing the tip image, whether or not an integral function is actually used.

The other alternative method is to map the values of the light transmittance of the "unknown" tip over a two dimensional representation and comparing that against such mapped values for a tip having only liquid present only where it should be, so that any significant deviation, hereinafter a "deviant value", can be flagged.

In either method, since various portions of the tip are scanned and individual algorithms are used for each portion, the presence of air bubbles, if any, is more readily detected at the individual portions, than is the case if the scanner took one single but complete scan of the entire tip, and a single algorithm is used.

As is well-known, the values of the light transmission are expressed as voltages produced by the detector. Furthermore, the use of absorption values instead of the light transmission still uses the measurement of transmission, since absorption is determined as the inverse of the light transmitted through a tip with liquid present.

It is the above noted step of subtracting the light transmission of the "blank", that is, an empty tip, that allows the CCD array hereinafter described, to avoid in the FIG. 2 embodiment the problems noted above in the "Background" with digital cameras. Likewise, it is the comparison of the mapped values of the "unknown" tip, that is, the one containing liquid of unknown conditions, against mapped values of a tip perfectly filled with liquid, that again allows a CCD array to be used for the mapping while avoiding the problems of the digital camera noted above in the "Background".

Figure 1:
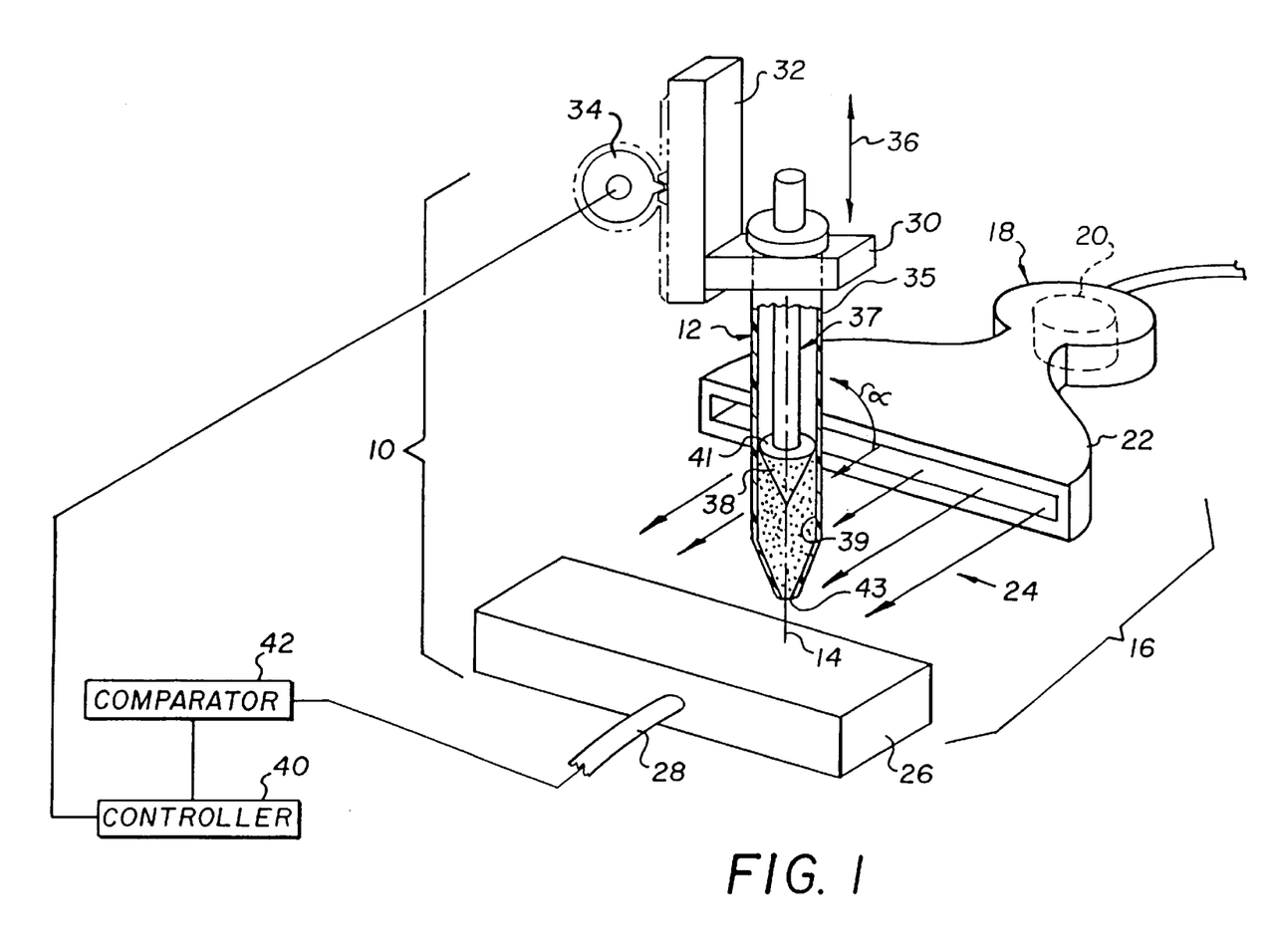
FIG. 1 is a fragmentary isometric view of preferred apparatus of the invention, demonstrating also the method of the invention.

Referring next to FIG. 1, the detecting apparatus 10 of the invention for detecting improper liquid in a metering tip 12 having an axis 14, used in an otherwise conventional clinical analyzer, comprises a scanner 16 which in turn comprises a light source 18, such as an LED 20 that illuminates a light guide 22 to direct a linear beam 24 across a span to a detector 26, which is preferably a conventional linear CCD array, the LED and array being constructed to emit and detect, respectively, light of one or more wavelengths between about 630 and 2000 nm. Below 630, there is too much interference from the absorption caused by bilirubin and hemoglobin. A highly preferred wavelength is 880 nm. Detector 26 in turn transmits via line 28 a signal in volts that represents the light that is transmitted in inverse proportion to the amount of liquid that intercepts the beam 24.

Additionally, to provide relative motion of a mounted pipette tip 12, a tip holder 30 mounts tip 12 and is connected to an elevator such as rack 32 and drive pinion 34 driven by a conventional motor, not shown, to move tip 12, arrow 36, past beam 24 to allow scanner 16 to scan the tip at each vertical portion along axis 14, at an angle alpha where alpha is generally 90 degrees, that is, generally normal to the tip axis 14. As used herein, "generally" when applied to this context means, plus or minus 10 degrees.

Thus, scans are obtained for tip portions spaced vertically along the tip axis. An example of the spacing of the portions is a distance of between about 0.001 mm and about 1 mm.

Any tip 12 can be used, but preferably it includes a hollow body 35 and an interior, electrically conductive plunger 37 driven along axis 14 by a conventional motor, not shown. Plunger 37 is conventional and includes a cone 38 that wipes against the inside surface 39 of tip 12 at a wipe line 41, to create partial vacuum or partial pressure to aspirate in or drive out liquid (shown as speckles in FIG. 1). Plunger 37 is electrically conductive so as to be able to detect, when cone 38 is at the bottom of tip 12, liquid levels of the container from which liquid is to be aspirated.

Still further, a conventional controller 40 is connected to the motor driving gear 34, to ensure that signals collected by a conventional comparator 42 are collected for a plurality of adjacent portions of the tip representing all levels within the tip where liquid should be present, including just below aperture 43 of the tip where a drop of liquid might be pendant, and just above where liquid should be. Comparator 42 in turn compares the light transmitted through a tip of "unknown" condition, with the light transmission known to exist for the same tip containing bubble-free liquid at each of the adjacent portions of the tip, that is, liquid in contact with and below cone 38. It further includes in memory a chart or plot of known transmission values representing the same tip when either a) no liquid is present and cone 38 is at its raised position that otherwise represents a tip full with liquid, and b) when tip 12 has either liquid pendant from tip 12 or above cone 38.

As is readily apparent, controller 40 and comparator 42 are preferably and conveniently both part of electronics well-known to those skilled in the art.

In the method of the invention, one alternative noted above produces the result of FIG. 2. That is, using preferably the apparatus of FIG. 1, liquid is first aspirated into tip 12 to nominally fill it, as shown in FIG. 1. Tip 12 is then lowered, arrow 36, to scan the tip with beam 24. (Alternatively, but this is more cumbersome, tip 12 can be maintained stationary and scanner 16 moved relative to it.) As tip 12 passes through beam 24, comparator 42 receives transmission signals for each of the several positions within tip 12 where liquid nominally exists, that is, from the lowest position in tip 12 up to the point where cone 38 is in wiping contact with side surface 39. A transmission signal is also received for a position below the tip to detect any pendant drop, as well as above the cone-wiping position to detect whether liquid has been improperly ejected above the cone.

From each tip portion signal, comparator 42 "subtracts" out the transmission signal produced by a dry tip but with plunger 37 in the same raised position, and an absolute value of the difference signal is produced.

The absolute value of the difference signal noted above is integrated, or summed, over all the scanning positions, to obtain a total value of transmittance due solely to the liquid (the dry tip "blank" values having been subtracted).

At this point, the plot of FIG. 2 is useful. FIG. 2 is a calibration plot of the integrated absolute values of transmission for the tip in question and is obtained by plotting the values of transmission less the subtracted dry-tip blank values of each portion scanned, integrated over the entire tip from aperture 43 to wipe line 41, for either a) 4 microliters of liquid and 6 microliters of air bubbles, b) 7 microliters of liquid and 3 microliters of air, c) 9 microliters of liquid and 1 microliter of air, d) 10 microliters of liquid and no air bubbles, and e) 13 microliters of liquid and no air bubbles. Only the absolute values so integrated are plotted. In actuality, the x-axis values are negative, since the dry-tip blank transmission values are greater than the transmission values with liquid present. For a particular tip similar to that shown in FIG. 1, this produced a best-fit straight line having an equation of $y=0.1127x+1.5257$. As is apparent, this plot is previously obtained and stored in comparator 42.

Comparator 42 then takes the reading for the tip of "unknown" condition, and locates the summed absolute value of the signal on the x-axis. For this particular plot, if the intersect is not at the point produced by a summed signal of 75.2 volts ±7 volts, which is the value on the dashed line for 10 microliters of liquid, then the signal is representative of an error in that the nominal liquid volume of 10 $\mu$L and zero air bubbles is not present.

This graph of course represents a look-up table in the analyzer, and the microprocessor therefor need only take the voltage of the transmission values and determine if it is within ±7 volts of 75.2.

It will be readily apparent that the tolerated deviation of ±7 volts does exclude the value of 67 volts, which represents 9 microliters of liquid and 1 of air, and the value of 83 volts, which represents 11 microliters of liquid. Both of these are errors and are to be flagged as such.

As will be appreciated, the unacceptable deviations of cases a), b), and c) noted above, producing less than the expected absolute values of voltage are to be expected. That is, the numbers are actually negative voltages, due to the blank subtraction. If no liquid were present, the absolute value goes to zero, and the more liquid present, the more negative the value and the larger the absolute value.

However, the plot of FIG. 2 does not account for any liquid pendant from the tip below aperture 43, nor liquid squeezed past plunger 37 above wipe line 41. To detect these errors, in addition to comparing the actual reading against the reading predicted from FIG. 2, the scans taken below aperture 43 and above wipe line 41 are examined, either before or after subtracting the dry-tip "blank" value. If they are not within a predetermined range of values for no liquid present, then the reading indicates an abnormality is present, and the tip reading is flagged as being in error, that is, not within the predetermined range of known total values for nominal liquid volumes. Again, the "nominal volume" is one in which no liquid appears below aperture 43 as a pendant drop or above wipe line 41.

Figure 3A:
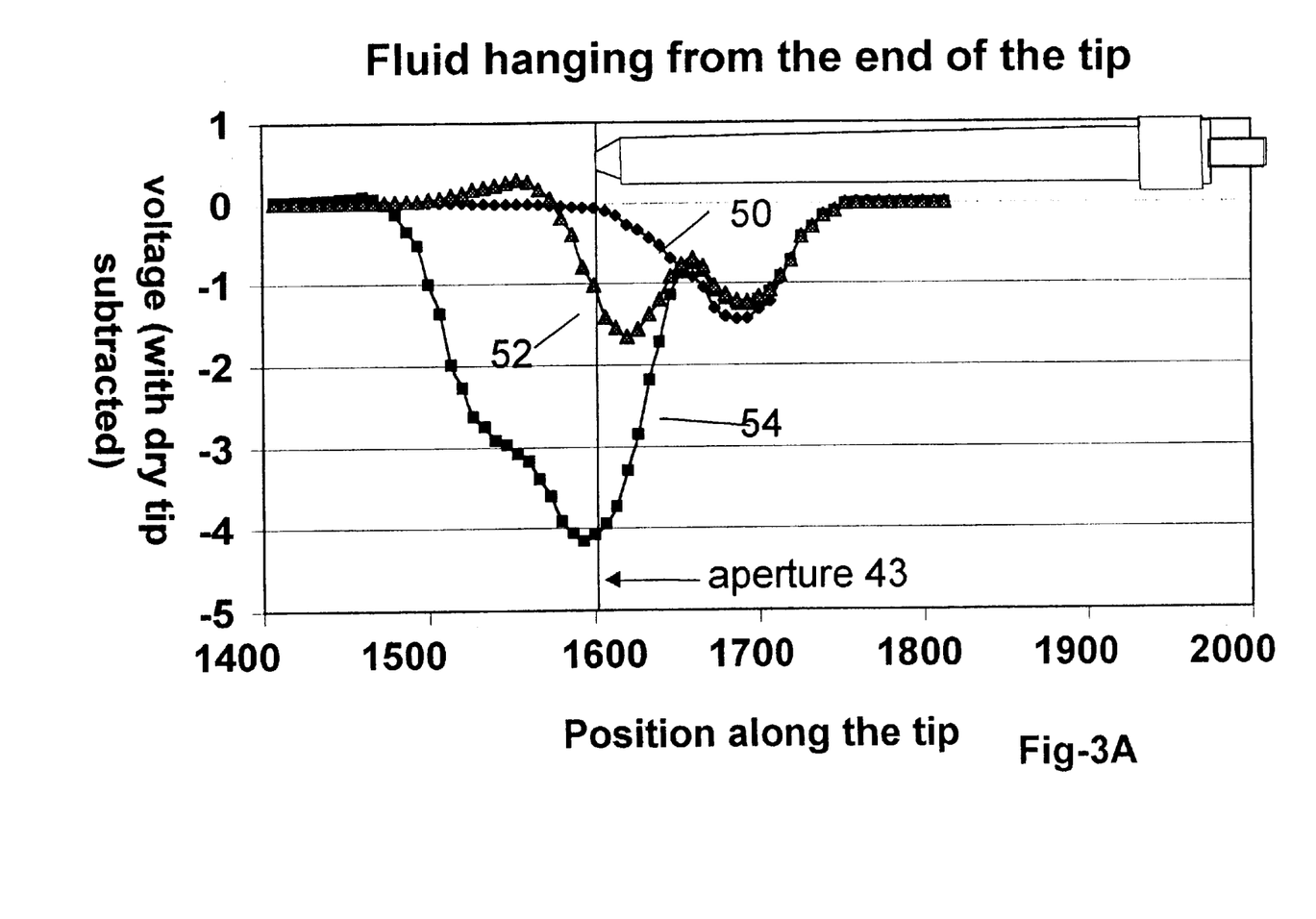
FIGS. 3A and 3B are plots of transmission voltages against the position scanned measured with respect to the aperture end of the tip, FIG. 3A being with the dry-tip blank values subtracted and FIG. 3B with them not subtracted.

FIGS. 3A and 3B illustrate the validity of the extra step of evaluating the scan below aperture 43. In the case of FIG. 3A, the dry-tip blank transmission values have been subtracted. (The numbers along the x-axis are arbitrary distance values.) A tip with no pendent drop produced curve 50, which, at the scan at or below aperture 43, gave a reading less than –0.5 volts. However, with a pendent drop of 3 $\mu$L, curve 52 shows a voltage value greater than –0.5 at and below aperture 43. That is, at aperture 43 the voltage reading is –1.0. Curve 54 represents a pendant drop of 5 $\mu$L. It is further estimated that a 1 $\mu$L pendent drop will produce a voltage value upon scanning at or below aperture 43, of –0.5 volts. Any pendant drop smaller than 1 $\mu$L in volume can be disregarded.

Thus, for the case where the dry-tip blank is subtracted, the predetermined range allowed for the scan below the tip aperture is an absolute value less than 0.5 volts.

Figure 3B:
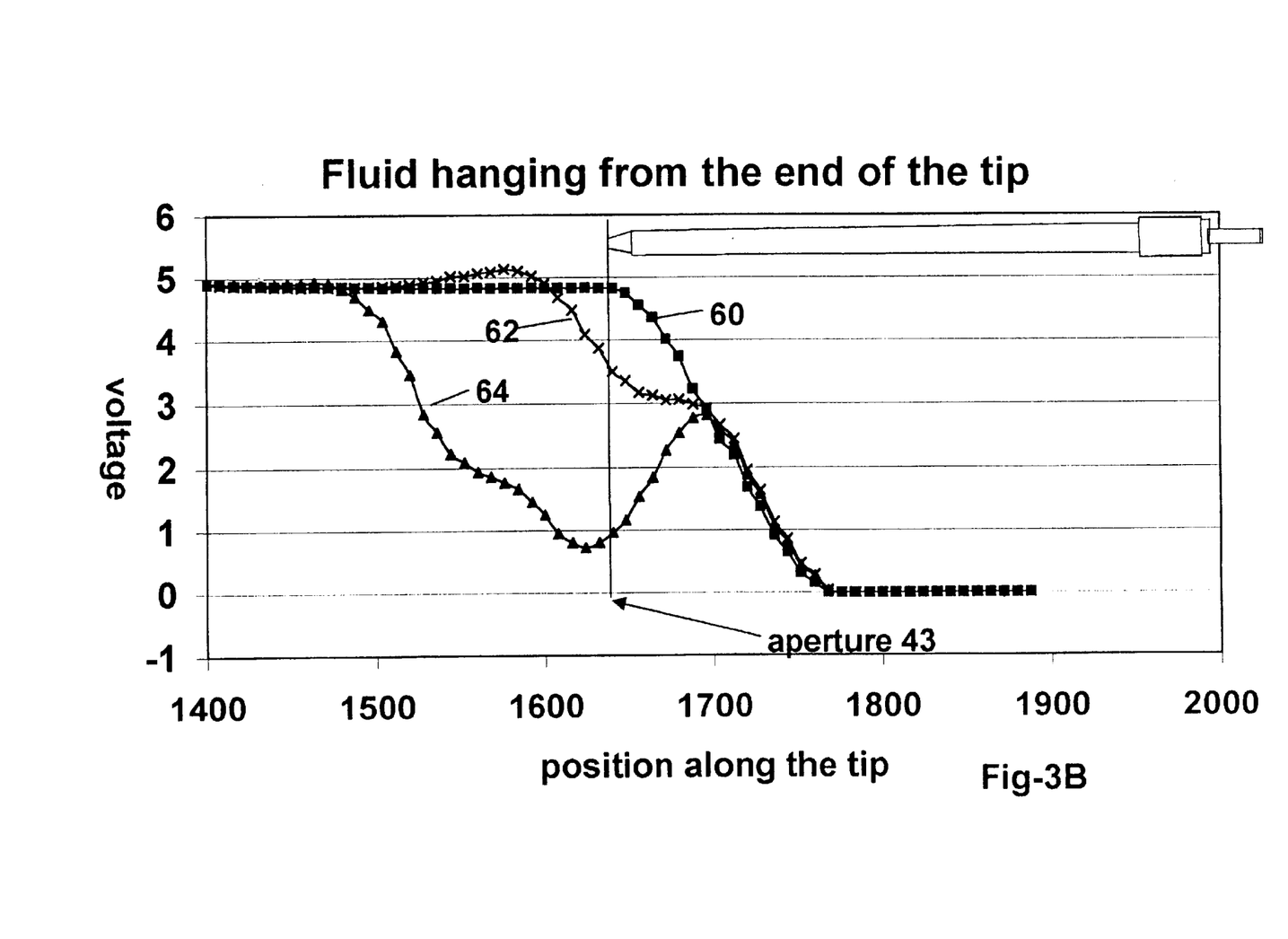

Similarly, for FIG. 3B, wherein no subtraction of the values of the dry-tip blank have occurred, curve 60 represents no pendant drop, producing a voltage value of 4.8–4.9 volts at or below aperture 43. However, a pendant drop of 3 $\mu$L produces, curve 62, a voltage value of 3.4 volts at aperture 43, and of 5 $\mu$L curve 64 produces a value of about 1.0 volts. It is expected a pendant drop of 1 $\mu$L will produce a value of about 4.5 volts. Hence the predetermined range of acceptable values is 4.6 to 4.9 volts. Anything outside of this when not subtracting a dry-tip blank is flagged as being in error.

FIGS. 4 through 12 are illustrative of an alternative technique for comparing the tip in an unknown condition with the transmission values for a tip with perfect conditions, that is, with liquid present only at levels between the aperture 43 and the wipe line 41, free of air bubbles. In this embodiment of the method of the invention, the actual transmission values in volts, detected for each portion by scanning as described above, is mapped over a two-dimensional representation of the tip in cross-section, and the map is compared with the map produced by a tip with liquid present under perfect conditions.

In each case, the map is representative of a cross-section taken generally vertically through axis 14 of the tip. Scans were all taken at 880 nm. The x-axis values are ± horizontal distances taken from axis 14, whereas the vertical axis values are distances vertically from an arbitrary zero point, which zero point is maintained even in FIGS. 10–11 that map a higher portion of the tip.

Also in each case, raw transmission values for the tip in question are presented, without the subtraction of values of a dry-tip blank. However, such subtraction could also be used before mapping, as another alternative embodiment.

Figure 4:
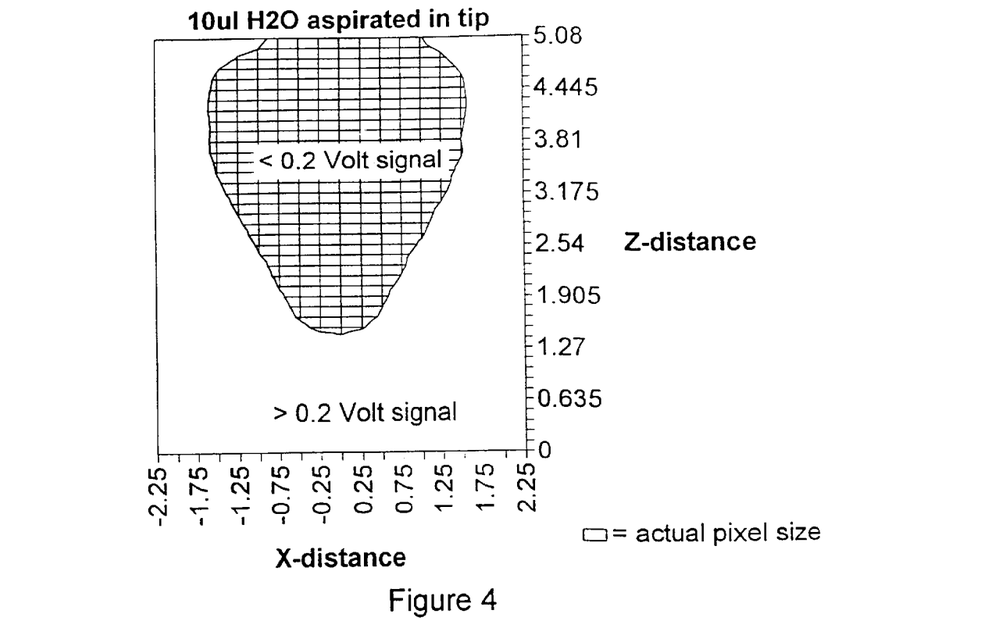
FIG. 4 is a computer-generated mapping of light transmittance in volts through the tip properly filled with liquid, plotted over the x and y axis extending along a tip cross-section taken through its axis.
Figure 5:
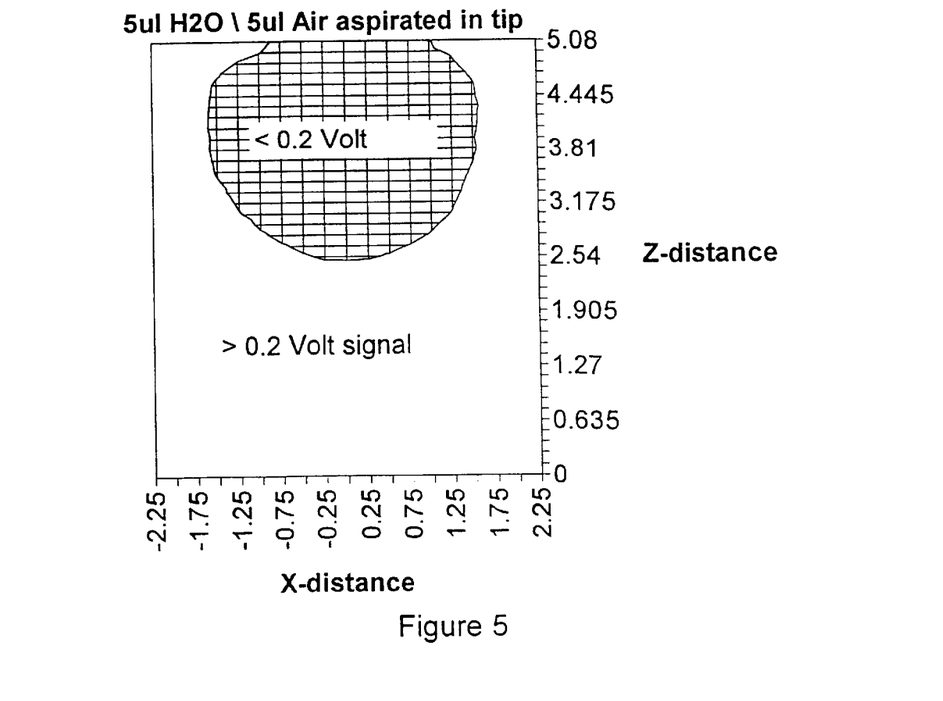
FIGS. 5 and 6 are mappings similar to that of FIG. 3, but illustrating the detectable map that occurs when various failure modes have occurred.

In FIG. 4, a mapped image is shown of a tip properly filled with liquid between aperture 43 and wipe line 41 with no air bubbles present. The curve that is shown is the boundary for transmission null voltages of less than 0.2 volts, representing just the liquid. This is to be contrasted with the mapped images of FIGS. 5 and 6. In FIG. 5, the tip was first filled with 5 $\mu$L of $H_2O$ and then 5 $\mu$L of air. The result is a large air bubble at the bottom portion of the tip just above aperture 43. The contour lines of the transmission voltage values show a marked loss of null voltages at the bottom portion, labeled ">0.2 volts".

Figure 6:
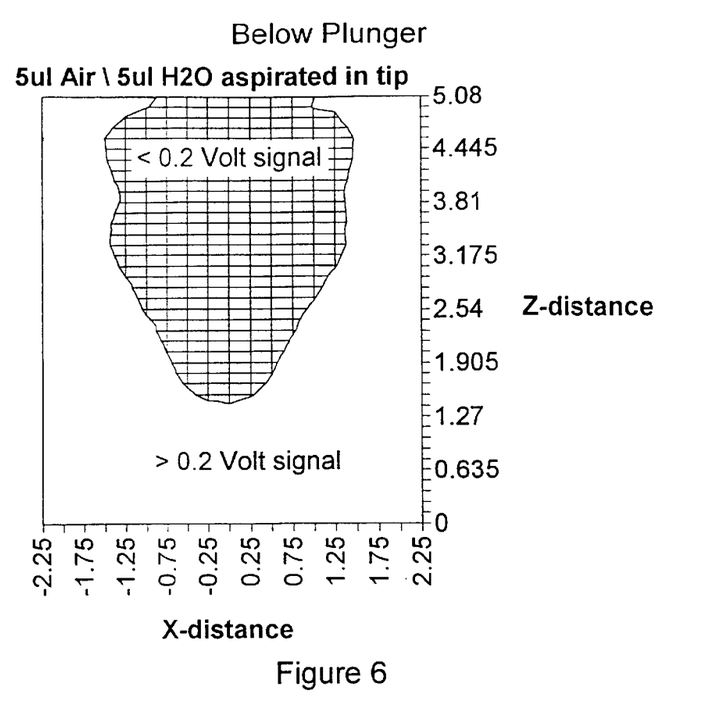

On the other hand, in FIG. 6, 5 $\mu$L of air was first aspirated, followed by 5 $\mu$L of $H_2O$, producing air bubbles in the upper portion just below wipe line 41. In this instance, the mapped null transmission voltage values (<0.2 volts) are necked-in at the upper portion, compared to the "perfect" map of FIG. 4.

In use, comparator 42 electronically compares the two dimensional maps of the unknown tip conditions and the perfect tip conditions, for deviations in the contour lines of the former, over the two dimensions, that exceed 0.1 volts. That is, the voltage values of the pixels of the test map are subtracted by the analyzer from the voltage values of the same pixels on the reference or "perfect" map, to determine if there is any difference value anywhere, that is greater than 0.1 volts.

Figure 7:
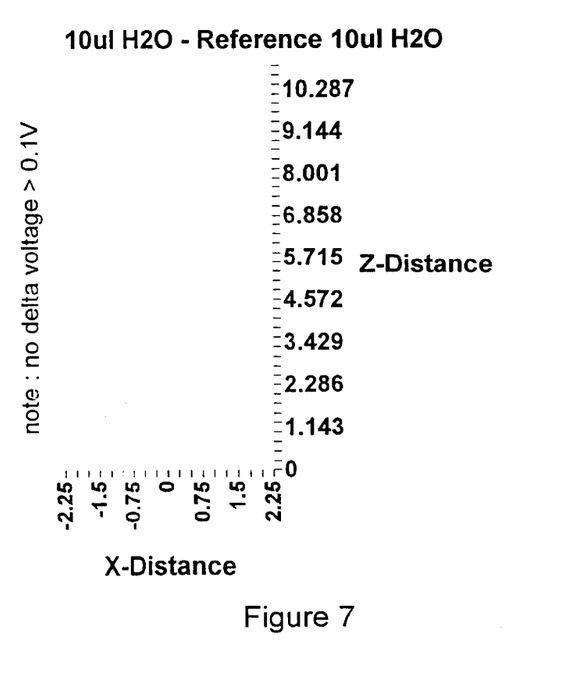
FIG. 7 is a plot of the subtraction voltages achieved when subtracting a plot similar to that of FIG. 4 for a perfect filled tip below the plunger, from the actual reference plot of FIG. 4.

FIG. 7 illustrates the comparison results in absolute values, wherein the tip was properly filled with no air bubbles. The test plot is not shown but was substantially identical to that of FIG. 4. Hence, FIG. 7 is a plot that has no data points, and represents a successful filling of the tip.

Figure 8:
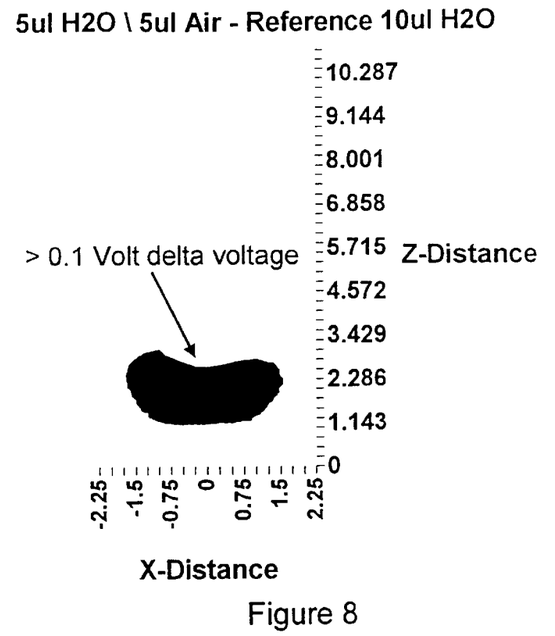
FIGS. 8 and 9 are plots similar to that of FIG. 7, but showing the results of subtracting the plots of FIGS. 5 and 6, respectively, from the plot of FIG. 4.
Figure 9:
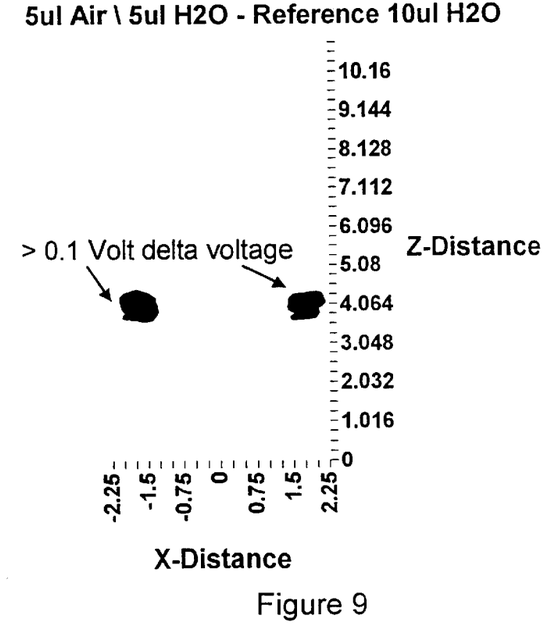

On the other hand, the comparison plot of FIG. 8, also in absolute values, shows a large area of >0.1 volt difference, precisely in the truncated area that is "missing" in FIG. 5. Similarly, FIG. 9 indicates in a comparison plot, delta or difference voltages >0.1 volts precisely at the areas of the necked in portion, FIG. 6. It is the presence of any data points in FIGS. 8 or 9 (stored as a look-up table in the microprocessor) that cause the analyzer to issue an error message.

Figure 10:
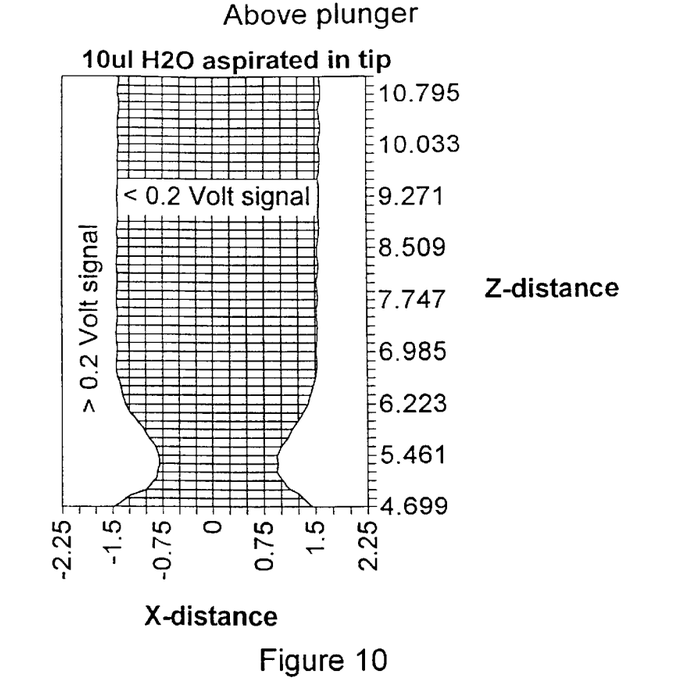
FIG. 10 is a mapping similar to that of FIG. 4, but showing only the region above the plunger in the absence of liquid.
Figure 11:
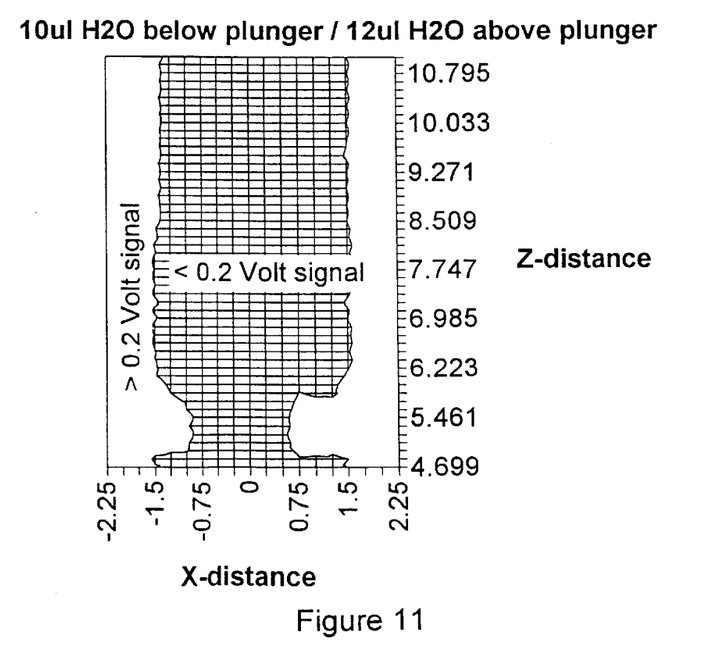
FIG. 11 is a mapping similar to that of FIG. 10, but illustrating the detectable map that occurs when liquid is erroneously present above the plunger.

Likewise, such two-dimensional mapping and comparisons are also useful to detect unwanted and unacceptable liquid above wipe line 41, FIGS. 10 and 11. FIG. 10 is a map similar to that of FIG. 4, but of the plunger portion of the tip above wipe line 41.

Importantly, the plunger portion of the tip represented by the map of FIG. 10 is free of any liquid above wipe line 41. In contrast, the tip portion mapped in FIG. 11, which likewise is the plunger portion above wipe line 41, has 12 $\mu$L of $H_2O$ above the wipe line. (The tips for both FIGS. 10 and 11 also had 10 $\mu$L of $H_2O$ below the wipe line.)

Figure 12:
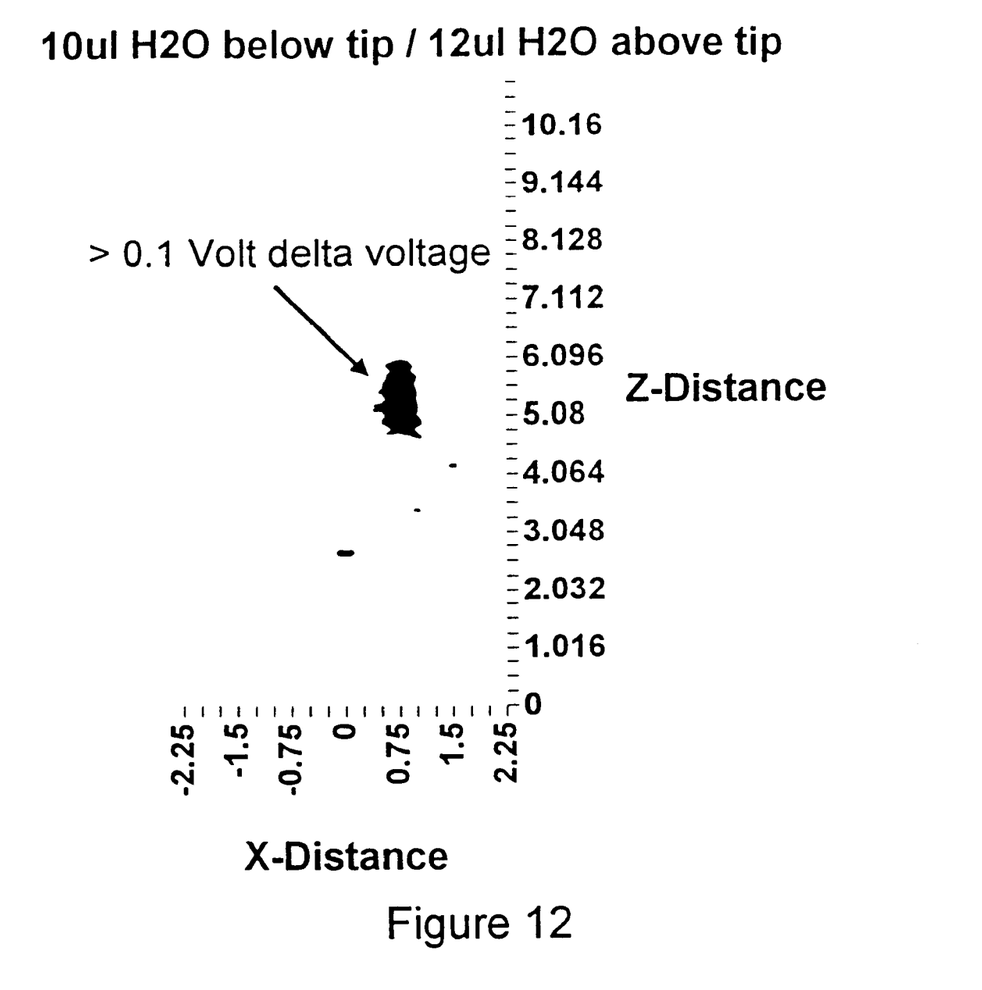
FIG. 12 is a subtraction plot similar to that of FIG. 8, when comparing the mapping of FIG. 11 with that of FIG. 10.

The map of the contour lines of FIG. 11 is readily different in appearance from that of FIG. 10. E.g., necking-in is noted at Z-distance 5.4, representative of liquid above wipe line 41. The comparison plot of FIG. 12 shows error data in four different clumps, representative of the visual differences between FIG. 11 and FIG. 10.

In this mapping technique of FIGS. 4 through 12, the transmission values were not detected for the scan below aperture 43. Instead, as shown the method of FIGS. 3A and 3B was used. However, mapping for drops pendant below aperture 43 could also be used.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. A method of detecting the status of aqueous liquid in a dispensing tip having an axis and being capable of transmitting light therethrough of radiation having wavelengths between about 630 and about 2000 nm, comprising the steps of:

a) aspirating the liquid into one of said tips to fill the tip to a nominal level;

b) scanning the liquid in said tip by a scanner comprising a light source and a light detector that emits and detects, respectively, radiation at one of said wavelengths;

c) providing relative motion between said tip and said scanner while said step b) is conducted, so that said scanner scans from a first position above where a pendant drop of the aqueous liquid would be located on said tip if present, to a predetermined second position which represents said nominal level;

d) while conducting steps b) and c), separately detecting at each of several portions of the tip between and including said first and second positions, the amount of light transmitted to said detector at said one wavelength, so that all liquid-containing levels within the tip are detected;

e) subtracting the amount of light transmitted in step d) from the amount transmitted through said tip when no liquid is present, for each of said several portions, to obtain a transmittance value caused by the amount of liquid present, in each of said portions;

f) integrating said transmittance values from step e) for each of said several portions to obtain a total value of transmittance, in said tip, due to liquid present;

g) comparing said total value of transmittance with total values known to exist for selected nominal liquid volumes free of air bubbles;

h) repeating steps c) and d) for a position below said first position where a pendant drop might be present and above said second position where extraneous liquid might be present;

i) comparing the value of light transmitted at both said below and above positions against a value transmitted with no liquid present at said below and above positions, respectively; and j) flagging the results as being in error if the comparison of step g) is not within a predetermined range for the selected nominal liquid volume, or if the comparison in step i) is not within a predetermined range of the value with no liquid present for either said below or above position.

2. A method of detecting the status of aqueous liquid in a dispensing tip having an axis and being capable of transmitting light therethrough of radiation having wavelengths between about 630 and about 2000 nm, comprising the steps of:

a) aspirating the liquid into one of said tips to fill the tip to a nominal level;

b) scanning the liquid in said tip by a scanner comprising a light source and a light detector that emits and detects, respectively, radiation at one of said wavelengths;

c) providing relative motion between said tip and said scanner while said step b) is conducted, so that said scanner scans from a first position below said tip where a pendant drop of the aqueous liquid would be located if present, to a predetermined second position above said first position that represents said nominal level;

d) while conducting steps b) and c), separately detecting at each of several portions of the tip between and including said first and second positions, the amount of light transmitted to said detector at said one wavelength, so that all liquid-containing levels within the tip are detected;

e) mapping said amounts of light transmitted over a two-dimensional representation of the tip cross-section taken through the tip axis;

f) comparing the mapped values against known mapped values for a tip containing liquid free of air bubbles, located only between said first and second positions; and g) flagging the results as being in error if the comparison of step f) detects a mismatch beyond a preselected deviant value.

3. A method as defined in claim 1 or 2, wherein said portions are spaced apart a distance that is between about 0.001 mm and 1 mm.

4. A method as defined in claim 1 or 2, wherein said one wavelength is about 880 nm.

5. A method as defined in claim 1 or 2, wherein said light source is an LED.

6. A method as defined in claim 1 or 2, wherein said scanning step directs said radiation at an angle to said tip axis that is generally 90°.

7. Apparatus for detecting improper liquid content of a metering tip of an analyzer, the tip having an axis, the apparatus comprising:

a) a scanner comprising a light source, a light detector, and means for transmitting light from said source to said detector at a wavelength which is between about 630 and about 2000 nm;

b) moving means for providing relative motion of one of said tips past said scanner so that said scanner scans said tip and its contents;

c) a controller of said moving means and said detector that directs said detector to detect light transmitted through the tip to said detector at at least several adjacent portions of said tip, as well as just below said tip where any pendant drop would be located; and d) a comparator that compares the light transmitted at said several levels with that known to represent the tip containing bubble-free liquid at each of said levels.

8. Apparatus as defined in claim 7, wherein said light source and light detector operate at about 880 nm.

9. Apparatus as defined in claim 7, wherein said scanner directs said radiation at an angle to said tip axis that is generally 90°.

10. Apparatus as defined in claim 7, and further including in combination, a metering tip and means for mounting said tip on said moving means, said tip comprising a hollow body and an electrically conductive plunger within said body.

11. A method of detecting the status of aqueous liquid in a dispensing tip having an axis of symmetry and which is capable of transmitting light therethrough of radiation between 630 and 2000 nm, comprising the steps of:

a) aspirating the liquid into one of said tips to fill the tip to a nominal level;

b) scanning the liquid in said tip by a scanner comprising a light source and a light detector, said source and detector being aligned along a direction that is generally normal to said tip axis;

c) providing relative motion between said tip and said scanner while said step b) is conducted, so that said scanner scans from a first position below said tip where a pendant drop of the aqueous liquid would be located if present, to a predetermined second position above said first position that represents said nominal level;

d) while conducting steps b) and c), separately detecting at each of several portions of the tip between and including said first and second positions, the amount of light transmitted to said detector, so that all liquid-containing levels within the tip are detected;

e) comparing said detected light of step d) with light known to be transmitted if liquid is present only at all of said levels, free of air bubbles; and f) flagging the results as being in error if water is detected at said first position; or if it is not detected because of air bubbles at any one of said levels within said tip up to and including said second position; or if it is detected above said second position.

* * * * *